United States Patent
Groszmann et al.

(10) Patent No.: US 11,534,547 B2
(45) Date of Patent: Dec. 27, 2022

(54) DRUG DELIVERY SYSTEMS AND METHODS WITH PRESSURE SENSITIVE CONTROL

(71) Applicant: AMGEN INC., Thousand Oaks, CA (US)

(72) Inventors: Daniel Eduardo Groszmann, Belmont, MA (US); Scott Robert Gibson, Granada Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 258 days.

(21) Appl. No.: 16/725,069

(22) Filed: Dec. 23, 2019

(65) Prior Publication Data
US 2020/0238005 A1    Jul. 30, 2020

Related U.S. Application Data

(60) Provisional application No. 62/796,363, filed on Jan. 24, 2019.

(51) Int. Cl.
*A61M 5/168*    (2006.01)
*A61M 5/145*    (2006.01)
*A61M 5/172*    (2006.01)
*A61M 5/142*    (2006.01)

(52) U.S. Cl.
CPC ........ *A61M 5/16836* (2013.01); *A61M 5/145* (2013.01); *A61M 5/1684* (2013.01);
(Continued)

(58) Field of Classification Search
CPC ............ A61M 5/16836; A61M 5/1684; A61M 5/16804; A61M 5/145; A61M 5/172;
(Continued)

(56) References Cited

U.S. PATENT DOCUMENTS 6,620,133 B1 * 9/2003 Steck ............... A61M 5/20 604/67
2011/0306929 A1 * 12/2011 Levesque ........... A61M 5/158 604/150

(Continued)

FOREIGN PATENT DOCUMENTS

CA    3052482 A1    9/2018
CA    3062323 A1    11/2018

OTHER PUBLICATIONS

Meritmedical, Meritrans, 2015, p. 2 (Year: 2015).*

(Continued)

*Primary Examiner* — Bhisma Mehta
*Assistant Examiner* — Phoebe Anne Staton
(74) *Attorney, Agent, or Firm* — Marshall, Gerstein & Borun LLP (57) ABSTRACT

Systems and methods for drug delivery with pressure sensitive control are disclosed. A drug delivery system may include a reservoir filled or fillable with a drug, a drug delivery device coupled to the reservoir to deliver the drug from the reservoir to a patient, a pressure sensor, an output device, and a controller. The controller may be configured to determine if the drug delivery device has completed delivering a dose of the drug to the patient, and if delivery of the dose of the drug is complete, to measure tissue back pressure using the pressure sensor. Subsequently, the controller may be configured to determine if the tissue back pressure is below a first predetermined value, and if so, control the output device at least once and/or control a mechanism to retract an administration member from the patient.

20 Claims, 4 Drawing Sheets

(52) U.S. Cl.
CPC ........ *A61M 5/16804* (2013.01); *A61M 5/172* (2013.01); *A61M 2005/14208* (2013.01); *A61M 2205/50* (2013.01)

(58) Field of Classification Search
CPC .... A61M 2005/14208; A61M 2205/50; A61M 2005/14252; A61M 5/14248; A61M 5/16854; A61M 2205/3344; A61M 2205/3331; A61M 2005/1588; A61M 5/1723; A61M 2005/1726; A61M 5/3157; A61M 5/31573; A61M 5/3234; A61B 5/15194

See application file for complete search history.

(56) References Cited

U.S. PATENT DOCUMENTS

| | | | | |
|---|---|---|---|---|
| 2014/0221965 | A1 | 8/2014 | Regittnig et al. | |
| 2017/0232204 | A1* | 8/2017 | Knapp .................. | G09B 19/00 604/66 |
| 2018/0318501 | A1* | 11/2018 | Hochman ............... | A61M 5/46 |

OTHER PUBLICATIONS

Wayback Machine Meritrans 212, screenshot (Year: 2022).*
Tactilus, Tactile Pressure Sensor, 2011, pp. 1-2 (Year: 2011).*
Wayback Machine Tactilus, screenshot (Year: 2022).*
International Application No. PCT/US2020/012480, International Search Report and Written Opinion, dated Apr. 20, 2020.

* cited by examiner

DRUG DELIVERY SYSTEMS AND METHODS WITH PRESSURE SENSITIVE CONTROL

CROSS-REFERENCE TO RELATED APPLICATION

Priority is claimed to U.S. Provisional Patent Application No. 62/796,363, filed Jan. 24, 2019, the entire contents of which are incorporated herein by reference.

FIELD OF DISCLOSURE

The present disclosure generally relates to drug delivery systems and, more particularly, to a drug delivery system whose operation is responsive to sensed condition(s).

BACKGROUND

Some drugs are administered in the form of a pill that is swallowed and then digested. In certain cases, however, it is desirable for a drug to be administered by means other than through the digestive track. Bypassing the stomach can prevent catalytic enzymes from degrading active ingredients in the drug and increases the likelihood that a necessary amount of a drug, at a desired concentration, reaches a targeted site. This form of delivery is referred to as parenteral delivery and has become more prevalent. This growth is partly the consequence of an increased number of treatments involving biologics, which in many cases are injected in liquid form.

Typically a drug injection involves the use of a drug delivery device having a reservoir and an administration member such as a hollow needle or cannula. A pointed end of the administration member is inserted into the patient and the reservoir is actuated to deliver the drug to the patient via the administration member. Considerable attention has been devoted to ensuring that such drug delivery devices are configured to deliver a prescribed volume or dose of a drug to the patient. This is because many treatments require the delivery of an exact amount of a drug, with even small variations being unacceptable. Under delivery can, for example, compromise the efficacy of the drug, while over delivery can increase the risk of adverse side effects, for example.

Self-injection with a drug delivery device introduces additional risk of suboptimal delivery. Patients who are not experienced with self-injecting or in a weakened state due to an illness, for example, are prone to operating the drug delivery device improperly. Further, even if the drug delivery device is operated according to its intended use, environmental and/or operating conditions including the patient's physiology can result in incomplete delivery.

As described in more detail below, the present disclosure sets forth drug delivery systems and related methods embodying advantageous alternatives to existing systems and methods, and that may address one or more of the challenges or needs mentioned herein, as well as provide other benefits and advantages.

SUMMARY

One aspect of the present disclosure provides a drug delivery system including a reservoir filled or fillable with a drug, a drug delivery device coupled to the reservoir to deliver the drug from the reservoir to a patient, a pressure sensor, an output device, and a controller. The controller may be coupled to the pressure sensor and the output device. Furthermore, the controller may be configured: (a) to determine if the drug delivery device has completed delivering a dose of the drug to the patient, and if delivery of the dose of the drug is complete, to measure tissue back pressure using the pressure sensor, and (b) to determine if the tissue back pressure is below a first predetermined value subsequent to (a), and if the tissue back pressure is below the first predetermined value, to control the output device at least once.

Another aspect of the present disclosure provides a method including: (a) operating a drug delivery device to deliver a dose of a drug to a patient; (b) determining if the drug delivery device has completed delivering the dose of the drug to the patient, and if delivery of the dose of the drug is complete, measuring tissue back pressure; and (c) determining if tissue back pressure is below a first predetermined value subsequent to (b), and if the tissue back pressure is below the first predetermined value, activating an output device at least once.

A further aspect of the present disclosure provides a drug delivery system including a reservoir filled or fillable with a drug, a drug delivery device coupled to the reservoir to deliver the drug from the reservoir to a patient, a pressure sensor, and a controller coupled to the pressure sensor and the drug delivery device. The drug delivery device may include an administration member insertable into the patient and a mechanism configured retract the administration member from the patient. The controller may be configured: (a) to determine if the drug delivery device has completed delivering a dose of the drug to the patient, and if delivery of the dose of the drug is complete, to measure tissue back pressure using the pressure sensor, and (b) to determine if the tissue back pressure is below a first predetermined value subsequent to (a), and if the tissue back pressure is below the first predetermined value, to control the mechanism to retract the administration member from the patient.

Yet another aspect of the present disclosure provides a method including: (a) inserting an administration member of a drug delivery device into a patient; (b) operating the drug delivery device to deliver a dose of a drug stored in a reservoir to the patient via the administration member; (c) determining if the drug delivery device has completed delivering the dose of the drug to the patient, and if delivery of the dose of the drug is complete, measuring tissue back pressure; and (d) determining if tissue back pressure is below a first predetermined value subsequent to (c), and if the tissue back pressure is below the first predetermined value, operating the drug delivery device to retract the administration member from the patient.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

A drug, also referred to herein as a medicament or drug product, may be injected or infused using a variety of different approaches, technologies, and systems. For example, a drug may be filled into a reservoir (or container) in the form of a syringe, and then the syringe may be used to manually inject the drug via a needle inserted into the patient. Alternatively, the drug may be filled into a reservoir in the form of a syringe or other appropriate primary container, e.g., a cartridge, and then the pre-filled syringe or other container may be combined with an autoinjector configured to automate movement of a plunger within a bore of the syringe or container, and optionally insertion of a needle into the patient. For example, the autoinjector may include a drive assembly (e.g., a motor, spring(s), propellant reservoir, etc.) that causes the container to move within a housing and/or the plunger to move within the bore of the container upon manipulation of an activation element (e.g., by depressing a button or retracting a needle guard). As a still further alternative, the drug may be filled into a reservoir, and the reservoir (prior to or after filling) may be combined with a wearable device with a mechanism for automatically inserting a needle and/or cannula into the patient and a drive assembly (which may take the form of, e.g., a motor, spring(s), propellant reservoir, etc.) for automatically actuating the reservoir. The wearable device may include a housing that is releasably attachable to a patient's skin to form an on-body drug delivery system, for example.

In whatever form the drug delivery system may take, an administration member such as a needle or cannula is inserted into the patient and a force is applied to expel the drug from the reservoir through the administration member into the patient's tissue (e.g., subcutaneous tissue, muscular tissue, etc.). The force applied must overcome both internal resistance within the drug delivery system and resistance from the patient's tissue as the tissue makes space for the injected volume of the drug. The resistance from the patient's tissue results in tissue back pressure. Tissue back pressure is present both during an injection and for a period of time following the injection. Tissue back pressure gradually decays over time as the tissue absorbs or accommodates the drug. Immediately following the injection, however, tissue back pressure can be significant. As a consequence, tissue back pressure can cause the drug to leak out of the skin at the injection site. This results in what is referred to as a "wet" injection, which is not desirable for patient experience. Furthermore, and more significantly, leakage (also referred to as back-flow or reflux) results in a smaller than intended dose of the drug being delivered to the patient. Drug efficacy can be compromised as a result.

Figure 1:
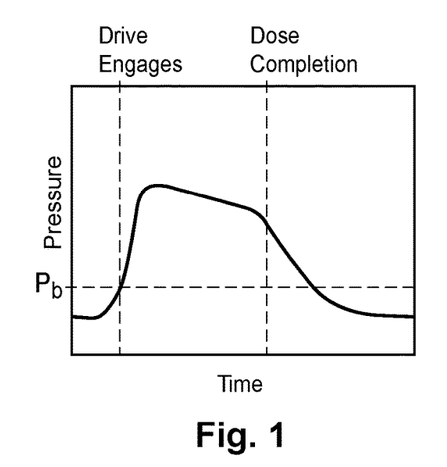
FIG. 1 is a graph illustrating how pressure varies over time during use of a drug delivery system in accordance with principles of the present disclosure.

FIG. 1 graphically illustrates an example of how pressure may vary over the duration of use of a drug delivery system to perform an injection. Here the pressure is being measured at a location within and/or along an internal fluid flow path of the drug delivery system. Initially, pressure may be equal to or substantially equal to ambient pressure (e.g., atmospheric pressure). Upon insertion of the administration member into the patient's tissue but before drug delivery begins, there may be a small rise in pressure due to tissue back pressure. This because an open end of the administration member may establish fluid communication between the internal fluid flow path of the drug delivery system and the interior of the patient's body before the start of drug delivery. Subsequently, upon engagement of a drive assembly to expel a dose of a drug from a reservoir of the drug delivery system to the patient, the pressure may rise significantly, as shown in the graph. Upon dose completion (e.g., when a stopper reaches an end-of-dose position), the pressure may begin to fall. However, it does not immediately return to ambient pressure due to the presence tissue back pressure. Tissue back pressure will persist until the patient's tissue has accommodated the injected dose of the drug. Thus, tissue back pressure can result in a leakage of the drug at the injection site post-injection if appropriate measures are not taken.

One way to inhibit or prevent leakage following an injection is to leave the administration member in place at the injection site until tissue back pressure falls below a certain threshold (identified in FIG. 1 as Pb). In some cases, Pb may be equal to approximately (e.g., ±10%) 0.5 pounds per square inch (psi). By leaving the administration member in place, it can act as a plug that prevents or inhibits the drug from leaking out through the hole formed in the skin by inserting the administration member. The time required for the tissue back pressure to fall below Pb may vary depending on, for example, delivery conditions and the patient's physiology. Accordingly, setting a fixed waiting period for the patient or drug delivery system to remove the administration member is usually not reliable way to prevent leakage.

Tissue back pressure tends to increase with higher injection rates. It is thought that this is caused by the tissue network experiencing higher mechanical strain in the case of high injection rates and consequently pushing back on the drug with more force. Certain drugs such as injectable biologics are experiencing a trend towards higher volume delivery. This, in part, is due to a trend towards less frequent dosing, which requires the delivery of a larger dose at any given injection. Larger doses, in turn, have been met with higher injection rates, in order to limit injection time. Accordingly, the trend towards higher volume delivery and the attendant higher injection rates has increased the likelihood of wet injections. Furthermore, certain drugs including injectable biologics are being produced in more viscous formulations than in the past. Higher drug viscosities tend to increase tissue back pressure and therefore increase the possibility of a wet injection.

This disclosure focuses on drug delivery systems that are sensitive to changes in pressure such as tissue back pressure, and considers those changes in controlling delivery of the drug and/or operation of the drug delivery system. As a consequence, the drug delivery system according to the present disclosure may alter its operation based on pressure levels to ensure that delivery of the drug is safe, predictable, and in accordance with a treatment regimen.

Figure 2:
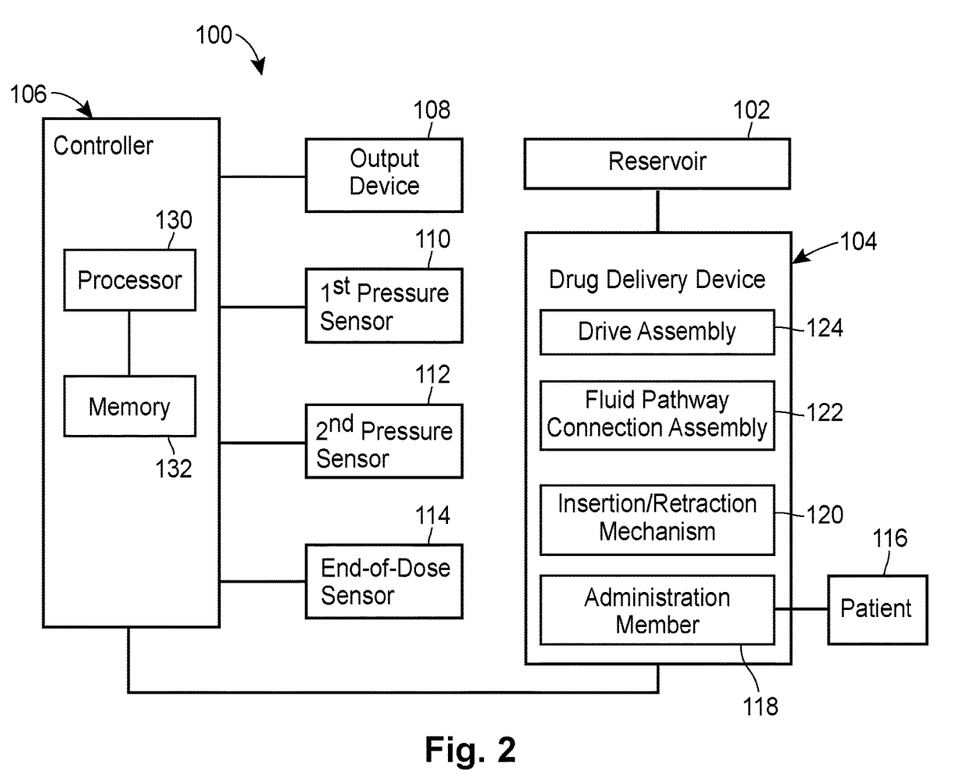
FIG. 2 illustrates a schematic view of a drug delivery system according to an embodiment of the present disclosure.

FIG. 2 is a schematic of a drug delivery system 100 according to one embodiment of the present disclosure. The drug delivery system 100 includes a number of components or subassemblies, such as a reservoir 102, a drug delivery device 104, a controller 106, an output device 108, a first pressure sensor 110, a second pressure sensor 112, and an end-of-dose sensor 114. These components or subassemblies may operate together to deliver a drug to a patient 116. The drug delivery system 100 may incorporate additional or fewer components or subassemblies relative to those depicted in FIG. 2. According some embodiments, for example, the output device 108, the first pressure sensor 110, the second pressure sensor 112, and/or the end-of-dose sensor 114 may be omitted.

It is noted that FIG. 2 is block diagram intended to show functional relationships and connections between various components or subassemblies and is not necessarily representative of the structure of those components or subassemblies. For example, although depicted as being separate from the drug delivery device 104, certain embodiments may require the drug delivery device 104 to structurally incorporate (e.g., enclose entirely or partially within a housing of the drug delivery device 104) one or more of the reservoir 102, controller 106, the output device 108, first pressure sensor 110, second pressure sensor 112, or the end-of-dose sensor 114, or any combination thereof. In some embodiments, the controller 106 and/or output device 108 may be part of an external or mobile computing device (e.g., a smartphone, smart watch, personal computer, remote server, etc.) that is separate from and portable relative to the drug delivery device 104.

The lines depicted in FIG. 2 indicate components or subassemblies which are coupled to each other. Those couplings can correspond to direct or indirect connections, and can be mechanical, electrical, chemical, electromechanical, and/or electrochemical in nature. The couplings between the controller 106 and other components or subassemblies in FIG. 2 may allow the controller 106 to communicate (e.g., via wired and/or wireless communications) information, data, and/or signals (e.g., analog and/or digital signals) with the other components or subassemblies, and those communications may be uni-directional or bi-directional. Additional or fewer interconnections than those depicted in FIG. 2 are possible.

The details of each of the components or subassemblies in FIG. 2 will be discussed below relative to a series of non-limiting examples.

The reservoir 102, which in some contexts may be referred to as a primary container, may be filled (e.g., pre-filled by a manufacturer) with a drug or fillable with a drug at the time of use of the drug delivery system 100. A stopper or other plunger member may be movable within the reservoir 102 to expel the drug from the reservoir 102 during use of the drug delivery device 104. The drug delivery device 104 may be coupled to the reservoir 102 to deliver the drug from the reservoir 102 to the patient 116. According to some embodiments, the patient 116 may use the drug delivery device 104 to self-inject or self-infuse a drug into his or her tissue as part of a therapeutic regimen. The drug delivery device 104 may include various components and subassemblies to assist with drug delivery including, by way of example and not limitation, an administration member 118, an insertion/retraction mechanism 120, a fluid pathway connection assembly 122, and a drive assembly 124.

The administration member 118 may be hollow and have a first end connected or connectable in fluid communication with the reservoir 102 via the fluid pathway connection assembly 122, and a second end to be inserted into the patient's tissue (e.g., subcutaneous tissue, muscular tissue, etc.). In some embodiments, the administration member 118 may take the form of a cannula (e.g., a blunt or soft cannula) made of a relatively flexible material and have a relatively blunt tip at the second end; whereas, in other embodiments, the administration member 118 may take the form of a needle made of a relatively rigid material and have a sharpened point at the second end.

The insertion/retraction mechanism 120 may be coupled to the administration member 118 and configured for automatically inserting and/or retracting the administration member 118 into and/or from the patient 116. In some embodiments, the insertion/retraction mechanism 120 may be coupled to and controllable via the controller 106 to insert and/or retract the administration member 118, e.g., in response to a condition or state of the drug delivery system 100 and/or patient 116 as determined by the controller 106. In some embodiments, the insertion/retraction mechanism 120 may be configured to move the administration member 118 from a retracted or storage position, wherein the administration member 118 is withdrawn entirely within an interior space of a housing of the drug delivery device 104, to a deployed or operative position, wherein an end of the administration member 118 extends beyond an exterior surface of the housing for insertion into tissue of the patient 116. Additionally or alternatively, the insertion/retraction mechanism 120 may be configured to retract the administration member 118 from the patient's tissue back into the interior space of the housing of the drug delivery device 104.

The fluid pathway connection assembly 122 may be configured to selectively establish fluid communication between the reservoir 102 and the administration member 118 via a sterile fluid flow path during use of the drug delivery device 104. The fluid pathway connection assembly 122 may include a first end connected or connectable in fluid communication with the reservoir 102, a second end connected or connectable in fluid communication with the administration member 118. Prior to use of the drug delivery device 104, the fluid pathway connection assembly 122 may not be in fluid communication with the reservoir 102. During setup of the drug delivery device 104, or during operation of the drug delivery device 104 but prior to drug delivery, the patient or a user may manually, or the drug delivery device 104 may automatically (e.g., under control of the controller 106), enable, connect, or open the necessary connections to establish fluid communication between the reservoir 102 and the administration member 118 via the fluid pathway connection assembly 122. Subsequently, the drive assembly 124 may actuate the reservoir 102 (e.g., push a stopper or plunger through the reservoir 102) to force the drug through the sterile fluid flow path of the fluid pathway connection assembly 122 and into the administration member 118 for delivery into the patient's tissue.

With continued reference to FIG. 2, the first pressure sensor 110 may be configured to detect at least tissue back pressure during use of the drug delivery device 104. According to some embodiments, the first pressure sensor 110 may be configured to detect fluid pressure within an internal fluid flow path of the drug delivery device 104 both (i) during a time period when the drive assembly 124 is operated to deliver a dose of the drug from the reservoir 102 to the patient 116 and (ii) during a time period after delivery of the dose is complete. During operation of the drive assembly 124, the first pressure sensor 110 may detect pressure resulting from the force exerted on the drug by the drive assembly 124 and pressure resulting from the force exerted on the drug by the tissue of the patient 116, collectively referred to herein as drive pressure. After delivery of the dose of the drug is complete, the pressure (referred to herein as tissue back pressure) detected by the first pressure sensor 110 may correspond solely or primarily to that resulting from the force exerted on the drug by the tissue of the patient 116. The tissue back pressure measurement may be possible because the first pressure sensor 110 may remain in fluid communication with the interior of the patient's body at the injection site via the administration member 118 after dose completion and prior to removal of the administration member 118 from the patient 116. During this time period, a volume of residual fluid, including, e.g., bodily fluid, the drug, or a combination of both, may remain within the internal fluid flow path of the drug delivery device 104, or at least within the fluid flow path between the first pressure sensor 110 and the outlet of the administration member 118. As a consequence of being exposed to the residual fluid, the first pressure sensor 110 is able to make a tissue back pressure measurement.

In addition to or as an alternative to the pressure measurements described in the preceding paragraph, the first pressure sensor 110 may be configured to measure pressure within the internal fluid flow path of the drug delivery device 104 during a time period following activation of the insertion/retraction mechanism 120 to insert the administration member 118 into the patient 116 and prior to activation of the drive assembly 118 to expel the drug from the reservoir. Such a measurement may facilitate a determination of whether or not the administration member 118 has been successfully inserted into the patient's tissue. When the administration member 118 is initially inserted into the patient, but prior to operation of the drive assembly 124, the first pressure sensor 110 may detect an increase in pressure due to tissue back pressure. This pressure increase can be interpreted to correspond to successful insertion of the administration member 118 according to some embodiments.

The first pressure sensor 110 may be configured to detect pressures in a range between approximately (e.g., ±10%) 0-100 psi, or in a range between approximately (e.g., ±10%) 0-10 psi, or in a range between approximately (e.g., ±10%) 1-10 psi, or in a range between approximately (e.g., ±10%) 1-5 psi. In some embodiments, the maximum pressure detectable by the first pressure sensor 110 may be equal to or less than approximately (e.g., ±10%) 100 psi, or equal to or less than approximately (e.g., ±10%) 10 psi, or equal to or less than approximately (e.g., ±10%) 5 psi. Furthermore, in some embodiments the minimum pressure detectable by the first pressure sensor 110 may be equal to or less than approximately (e.g., ±10%) 0.5 psi. In some embodiments, the first pressure sensor 110 may be optimized for detecting tissue back pressures, which may be relatively low as compared to the drive pressures occurring during operation of the drive assembly 124 to inject the drug.

According to some embodiments, the first pressure sensor 110 may have first surface exposed to fluid pressure within an internal fluid flow path of the drug delivery device 104 and a second surface exposed to ambient pressure (e.g., atmospheric pressure). So configured, the first pressure sensor 110 may be able to measure the pressure within the internal fluid flow path of the drug delivery device 104 relative to ambient pressure. In some embodiments, the drug may come into direct contact with the first surface of the first pressure sensor 110 during use of the drug delivery device 104, though that is not required. In some embodiments, the first and second surfaces of the first pressure sensor 110 may be defined by opposite sides of a flexible diaphragm or membrane. The diaphragm may undergo elastic deformation or deflection when the pressure within the internal fluid flow path differs from ambient pressure. That elastic deformation can be interpreted to correspond to fluid pressure within the internal fluid flow path. This may involve the diaphragm interfacing with a resistive, capacitive, or other electrical element. A capacitive-type pressure sensor may involve the use of a thin diaphragm as one plate of a capacitor. Applied pressure may cause the diaphragm to deflect and the capacitance to change. The change in capacitance may be proportional to the applied pressure.

In a semiconductor-based configuration, the first pressure sensor 110 may include a piezo-resistive pressure measuring cell including a thin silicon membrane. Disposed on the silicon membrane may be one or more, or four, resistors in the form of impurity atoms implanted in the silicon crystal lattice. When a pressure is applied to the silicon membrane, resistances change because of mechanical stress on the silicon membrane. This is commonly referred to as the piezo-resistive effect. The resistors may be connected in a Wheatstone bridge such that when supplied with an electrical potential, an electric output signal is generated that is proportional to the applied pressure. Other configurations of the first pressure sensor 110 are also possible.

Still referring to FIG. 2, in addition to or as an alternative to the first pressure sensor 110, the drug delivery system 100 may include the second pressure sensor 112. The second pressure sensor 112 may be configured to detect drive pressure during use of the drug delivery device 104. This may be accomplished in certain embodiments by configuring the second pressure sensor 112 to detect fluid pressure within an internal fluid flow path of the drug delivery device 104 during operation of the drive assembly 124 to expel a dose of the drug from the reservoir 102 to the patient. In some embodiments, the second pressure sensor 112 may have a physical configuration similar to any of those described above in connection with the first pressure sensor 110. Furthermore, in some embodiments, the second pressure sensor 112 may be mounted upstream of the first pressure sensor 110, although other mounting locations are possible too. The second pressure sensor 112 may be omitted in some embodiments.

Whereas the first pressure sensor 110 may be optimized for detecting relatively low tissue back pressures, the second pressure sensor 112 may be optimized for detecting relatively high drive pressures. In some embodiments, the second pressure sensor 112 may be configured to detect pressures in a range between approximately (e.g., ±10%) 10-1000 psi, or in a range between approximately (e.g., ±10%) 10-100 psi, or in a range between approximately (e.g., ±10%) 10-50 psi, or greater than or equal to (e.g., ±10%) 10 psi, or greater than or equal to (e.g., ±10%) 20 psi. In some embodiments, the maximum pressure detectable by the second pressure sensor 112 may be equal to or greater than approximately (e.g., ±10%) 50 psi, or equal to or greater than approximately (e.g., ±10%) 100 psi. Furthermore, in some embodiments the minimum pressure detectable by the second pressure sensor 112 may be equal to or greater than approximately (e.g., ±10%) 10 psi.

Consistent with the intended functions of the pressure sensors 110 and 112, in some embodiments, a minimum pressure detectable by the first pressure sensor 110 may be lower than a minimum pressure detectable by the second pressure sensor 112; and/or a maximum pressure detectable by the second pressure sensor 112 may higher than a maximum pressure detectable by the first pressure sensor 110.

While the embodiment in FIG. 2 utilizes the pressure sensors 110 and 112 for measuring, respectively, tissue back pressure and drive pressure, alternative embodiments may omit the pressure sensor 112 and instead rely on the pressure sensor 110 for measuring both tissue back pressure and drive pressure. Use of a single sensor to measure both tissue back pressure and drive pressure reduces the number of parts and can save costs in certain cases. In such alternative embodiments, the pressure sensor 110 may be able to resolve the relatively low pressures associated with tissue back pressure as well as the relatively high pressures associated with drive pressure. For example, the pressure sensor 110 may be configured to detect pressures in a range between approximately (e.g., ±10%) 0-100 psi; or a minimum pressure detectable by the pressure sensor 110 may be equal to or less than approximately (e.g., ±10%) 0.5 psi and a maximum pressure detectable by the pressure sensor 110 may be equal to or greater than 50 psi.

Referring to FIG. 2, the end-of-dose sensor 114 may be configured to output a signal indicative of a stopper or other plunger element within the reservoir 102 having reached an end-of-dose position. In the end-of-dose position, the stopper or other plunger element will have expelled an intended dose of the drug from the reservoir 102. In a bolus injector configuration of the drug delivery device 104, for example, the end-of-dose position may correspond to the stopper or other plunger element contacting and stopping at a proximally-facing surface at a distal end of the reservoir 102. In certain such embodiments, the end-of-dose sensor 114 may directly measure the position of the stopper or other plunger element within the reservoir 102 via optical means, electrical means, magnetic means, a physical contact switch, and/or any other suitable sensing technique. In certain such embodiments, the end-of-dose sensor 114 may be mounted on or adjacent to a distal end of the reservoir 102. In alternative embodiments, the end-of-dose sensor 114 may indirectly measure the position of the stopper or other plunger element within the reservoir 102 by monitoring the movement or position of an element used for driving the stopper or other plunger element such as a motor, spring, plunger rod, tether, etc. In an embodiment where a motor is being monitored, the end-of-dose sensor 114 may measure a rotational position of the motor via optical means, electrical means, magnetic means, a physical contact switch, an encoder, and/or any other suitable sensing technique.

The output device 108 may be any device suitable for conveying information to the patient 116 or user including a display (e.g., a liquid crystal display), a touchscreen, a light (e.g., a light emitting diode), a vibrator (e.g., an electromechanical vibrating element), a mechanical or color-changing flag member, a speaker, an alarm, and/or any other suitable device, or any combination thereof. As described below in more detail, the output device 132 may be controlled (e.g., activated or de-activated) to alert or inform the patient or user after dose completion that the tissue back pressure remains above a first predetermined value (e.g., Pb) and thus the patient or user should wait to remove the administration member 118 from the patient's tissue and/or to alert or inform the patient that the tissue back pressure has fallen below the first predetermined value and thus the drug delivery device can be removed from the patient's skin with little or no risk of drug leakage at the injection site.

The controller 106 may be configured to control the operation of various component(s) of the drug delivery system 100, including, for example, the insertion/retraction mechanism 120, the fluid pathway connection assembly 122, the drive assembly 124, and the output device 108. Further, the controller 106 may be configured to receive and/or process information, data, signals (analog and/or digital), or other output from the first pressure sensor 110, the second pressure sensor 112, the end-of-dose sensor 114, and/or other elements of the drug delivery system 100 and/or external elements. Furthermore, the controller 106 may be responsive to the output it receives from such element(s), and may be configured to automatically control the operation of certain element(s) such as the insertion/retraction mechanism 120, the fluid pathway connection assembly 122, the drive assembly 124, and/or the output device 108 according to the programming or other configuration of the controller 106.

The controller 106 may include and/or implement its operations via an electrical device (e.g., a hardwired circuit, a microprocessor, etc.), a combination of electrical devices, a mechanical device, a combination of mechanical devices, a chemical device, a combination of chemical devices, or any combination thereof (e.g., an electromechanical device, an electrochemical device, etc.). According to those embodiments wherein the controller 106 includes a microprocessor or the like, the configuration of the controller 106 may correspond to the software or other programming of the controller 106. In some embodiments, the controller 106 may be pre-configured by a manufacturer and/or healthcare provider such that it cannot later be reconfigured by the patient or other end user; whereas, in other embodiments, the controller 106 may be configurable by any individual or entity, within reason.

In some embodiments, the controller 106 may be provided as a computing device that includes a processor 130 (or multiple processors) and a memory 132 (or multiple memories) in communication with or integrated with each other. The processor 130 may include, for example, one or more of a microprocessor, micro-controller, programmable logic controller, digital signal processor, microcomputer, central processing unit, field programmable gate array, logic circuitry, analog circuitry, digital circuitry, software-based processing module, and any device that manipulates signals (analog and/or digital) based on hard coding of the circuitry and/or operational instructions, or any combination thereof. The memory 132 may include a non-transitory computer-readable storage medium configured to store data, including, for example, non-transitory computer-readable instructions constituting one or more services, programs, and/or modules and any data operated on or produced by such services, programs, and/or modules. The memory 132 may store the data on a volatile (e.g., random access memory (RAM), etc.) and/or non-volatile memory (e.g., a hard disk), and may be a removable or non-removable memory. The one or more processors may be configured to fetch and execute the instructions stored in the one or more memories in order to perform or implement various functions of the drug delivery system 100, including, for example, controlling the drive assembly 124 to deliver the drug to the patient 116 according to a dosing regimen, controlling the insertion/retraction mechanism 120 to insert the administration member 118 into the patient and/or retract the administration member 118 from the patient, and/or controlling the output device 108.

According some embodiments, the controller 106 may be coupled (e.g., via wired or wireless connections) with one or more of the insertion/retraction mechanism 120, the fluid pathway connection assembly 122, the drive assembly 124, the output device 108, the first pressure sensor 110, the second pressure sensor 112, and the end-of-dose sensor 114 such that the controller 106 can transmit communications to and/or receive communications from one or more of the insertion/retraction mechanism 120, the fluid pathway connection assembly 122, the drive assembly 124, the output device 108, the first pressure sensor 110, the second pressure sensor 112, and the end-of-dose sensor 114. Such communications may be electrical and/or mechanical in nature, and/or may include information, data, and/or signals (analog and/or digital).

According to some embodiments, the controller 106 may be configured to analyze the output (e.g., signals, data, information, etc.) received from the first pressure sensor 110, second pressure sensor 112, and/or end-of-dose sensor 114 and make determinations about the operational state or condition of the drug delivery system 100 and/or the patient 116 based on the received output. Then, based on those determinations, the controller 106 may control or operate various elements of the drug delivery system 100 in accordance with a routine, program, regimen, etc. for which the controller 106 has been configured.

Figure 3:
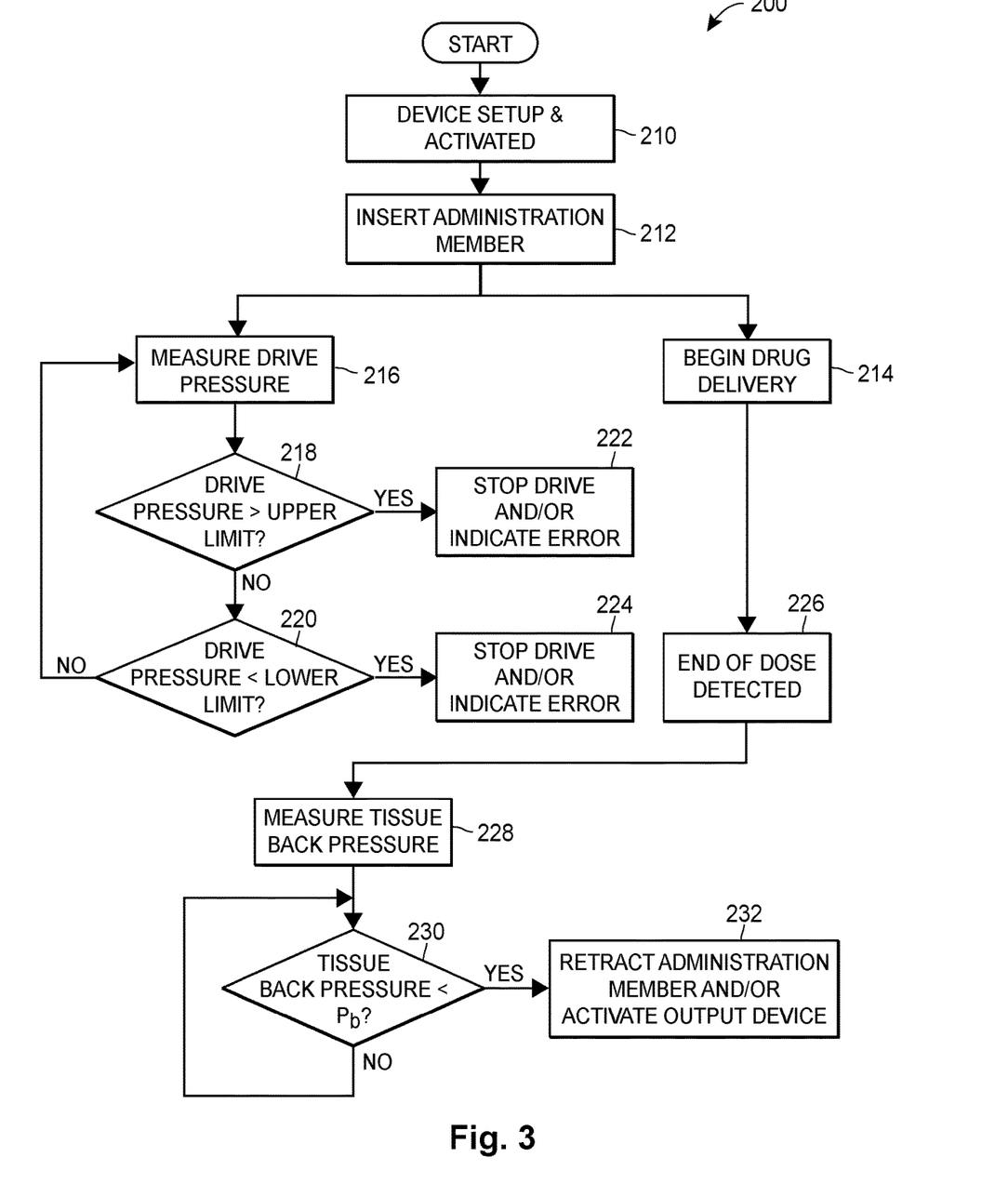
FIG. 3 is a block diagram of the operation of a drug delivery system such as illustrated in FIG. 2 according to an embodiment of the present disclosure.

An embodiment of a method 200 of operating a drug delivery system such as the one illustrated in FIG. 2 will now be described. Initially, the drug delivery device 104 may be set up and activated at block 210. In some embodiments, this step may involve removing the drug delivery device 104 from sterile packaging and/or, where the drug delivery device 104 is not preloaded with a pre-filled reservoir, filling a reservoir of the drug delivery device 104 with a drug or installing a pre-filled cartridge or syringe within a housing of the drug delivery device 104. Furthermore, in embodiments where the drug delivery device 104 is an on-body injector, this step may involve adhering or otherwise releasably attaching a housing of the drug delivery device 104 to the surface of the patient's skin, and then activating the drug delivery device 104, e.g., by pressing a button. In other embodiments where the drug delivery device 104 is an autoinjector or pen-type injector, this step may involve pressing a distal end of the drug delivery device 104 against the surface of the patient's skin while holding a proximal end of drug delivery device 104 in one's hand, and then activating the drug delivery device 104, e.g., by pressing a button.

Next, at block 212, the insertion/retraction mechanism 120 may automatically, or the patient or user may manually, insert the administration member 118 into the patient's tissue by causing an end administration member 118 to penetrate through the surface of the patient's skin. In some embodiments, the insertion/retraction mechanism 120 may move the administration member 118 from a retracted or storage position, wherein the administration member 118 is withdrawn entirely within an interior space of a housing of the drug delivery device 104, to a deployed or operative position, wherein an end of the administration member 118 extends beyond an exterior surface of the housing for insertion into the patient's tissue. As described below and with reference to FIG. 4, in some embodiments the controller 106 may perform a check to determine if the administration member 118 has been properly inserted into the patient's tissue following activation of the insertion/retraction mechanism 120.

After insertion of the administration member 118, the drug delivery device 104 may begin delivering the drug to the patient 116 via the administration member 118 (block 214) and simultaneously, or shortly thereafter, begin measuring drive pressure (block 216) via the second pressure sensor 112. In alternative embodiments where the second pressure sensor 112 is omitted, the drive pressure measurement made be made via the first pressure sensor 110. At block 214, the drive assembly 124 may be activated, e.g., via the controller 106, to actuate the reservoir 102 and thereby expel a dose of the drug through the fluid pathway connection assembly 122 and then into the patient's tissue via the administration member 118. In embodiments where the drug delivery device 104 is a single bolus injector, the expelled dose of the drug may correspond to all or substantially all of the volume of the drug included in the reservoir 102. In other embodiments, the expelled dose of the drug may correspond to only a portion of the volume of the drug included in the reservoir 102. During operation of the drive assembly 124 to deliver the drug to the patient, the first pressure sensor 110 and/or the second pressure sensor 112 may be used to continuously or intermittently detect the drive pressure within an internal fluid flow path of the drug delivery device 104 and output a signal(s) representative of that pressure to the controller 106. Subsequent to block 216, and based upon the drive pressure signal(s), the controller 106 may be configured to determine (e.g., in the case of an electrical embodiment, be programmed to determine) if the drive pressure exceeds an upper limit (also referred to herein as a second predetermined value) at block 218 and/or is below a lower limit (also referred to herein as a third predetermined value) at block 220.

If the drive pressure is determined to exceed the upper limit, the controller 106 may automatically control the drive assembly 124 to stop actuating the reservoir 102 such that the drug delivery device 104 ceases delivering the drug to the patient at block 222. Additionally or alternatively, if the drive pressure is determined to exceed the upper limit, the controller 106 may automatically control (e.g., activate or de-activate) the output device 108 to inform or alert the patient or user that the drug delivery device 104 has malfunctioned or otherwise indicate that an error has occurred at block 222.

If the drive pressure is determined to be below the lower limit, the controller 106 may automatically control the drive assembly 124 to stop actuating the reservoir 102 such that the drug delivery device 104 ceases delivering the drug to the patient at block 224. Additionally or alternatively, if the drive pressure is determined to be below the lower limit, the controller 106 may automatically control (e.g., activate or de-activate) the output device 108 to inform or alert the patient or user that the drug delivery device 104 has malfunctioned or otherwise indicate that an error has occurred at block 224.

Throughout operation of the drive assembly 124 to discharge the drug from the reservoir 102, the end-of-dose sensor 114 may monitor whether a stopper or other plunger element within the reservoir 102 has reached an end-of-dose position. When that occurs (block 226 in FIG. 3), the end-of-dose sensor 114 may output an end-of-dose signal(s), e.g., to the controller 106. Subsequent to block 226 and/or in response to the end-of-dose signal(s), the controller 106 may begin to monitor whether tissue back pressure is below the first predetermined value (e.g., Pb in FIG. 1). The controller 106 may make this determination based on a tissue back pressure signal(s) that is output from the first pressure sensor 110 at block 228. The first pressure sensor 100 may begin to output the tissue back pressure signal(s) at the start or drug deliver delivery, or alternatively, only after the end-of-dose detection. Based on upon the back pressure signal(s), the controller 106 may be configured to determine (e.g., in the case of an electrical embodiment, be programmed to determine) if the tissue back pressure is below the first predetermined value at block 230. If the tissue back pressure is determined to below the first predetermined value, the controller 106 may automatically control the insertion/retraction mechanism 120 to retract the administration member 118 from the patient's tissue and, for example, back into the interior space of a housing of the drug delivery device 104 at block 232. Additionally or alternatively, if the tissue back pressure is determined to be below the first predetermined value, the controller 106 may automatically control (e.g., activate or deactivate) the output device 108 to inform or alert the patient or user that drug delivery is complete and/or that it is safe to remove the drug delivery device 104 from the patient's skin at block 232.

If the tissue back pressure is determined by the controller 106 to exceed the first predetermined value at block 230, the controller 106 may continue to monitor the tissue back pressure as shown in FIG. 3, and, in certain embodiments, may automatically lock the insertion/retraction mechanism 120 to prevent retraction the administration member 118 and/or automatically control (e.g., activate or deactivate) the output device 108 to inform or alert the patient or user that drug delivery is not yet complete and/or to wait to remove the drug delivery device 104 from the patient's skin.

Further refinements may be included in any of the foregoing embodiments.

Figure 4:
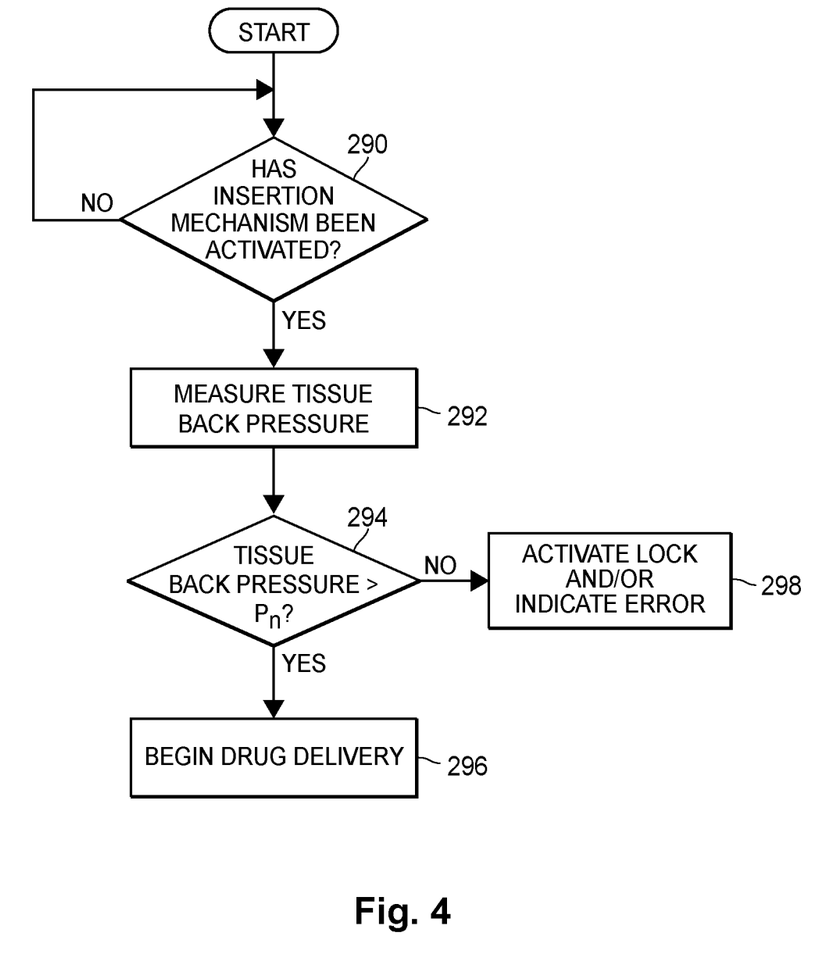
FIG. 4 is a block diagram of the operation of a drug delivery system such as illustrated in FIG. 2 according to another embodiment of the present disclosure.

For example, in some embodiments, the first pressure sensor 110 and/or the second pressure sensor 112 may be used to determine whether the administration member 118 has been properly inserted into the patient's tissue prior to the start of drug delivery. This is possible because there may be a slight rise in pressure within the internal fluid flow path of the drug delivery device 104 upon insertion of the administration member 118 into the patient's tissue as a consequence of tissue back pressure. This rise in pressure can be interpreted as an indication that the administration member 118 has been properly inserted into the patient's tissue. According to such embodiments and as illustrated in FIG. 4, the controller 106 may be configured to determine (e.g., in the case of an electrical embodiment, be programmed to determine) if the insertion/retraction mechanism 120 has been activated to insert the administration member 118 into the patient's tissue at block 290. Subsequent to block 290 and if the insertion/retraction mechanism 120 has been activated, the controller 106 may, based on signal(s) output by the first pressure sensor 110 and/or the second pressure sensor 112, be configured to determine (e.g., in the case of an electrical embodiment, be programmed to determine) if tissue back pressure exceeds a fourth predetermined value ($P_n$ in FIG. 4) at blocks 292 and 294. If the tissue back pressure is determined to exceed the fourth predetermined value, the controller 106 may automatically control (e.g., activate) the drive assembly 124 to actuate the reservoir 102 to deliver the dose of the drug to the patient at block 296. Additionally or alternatively, if the tissue back pressure is determined to exceed the fourth predetermined value, the controller 106 may automatically control (e.g., activate or deactivate) the output device 108 to inform or alert the patient or user that drug delivery is underway or about to begin at block 296.

If the tissue back pressure is determined by the controller 106 to be below the fourth predetermined value, the controller 106 may automatically lock the drive assembly 124 to prevent actuation of the reservoir 102 to discharge the drug and/or automatically control (e.g., activate or deactivate) the output device 108 to inform or alert the patient or user of device malfunction or otherwise indicate that an error has occurred at block 298.

Figure 5:
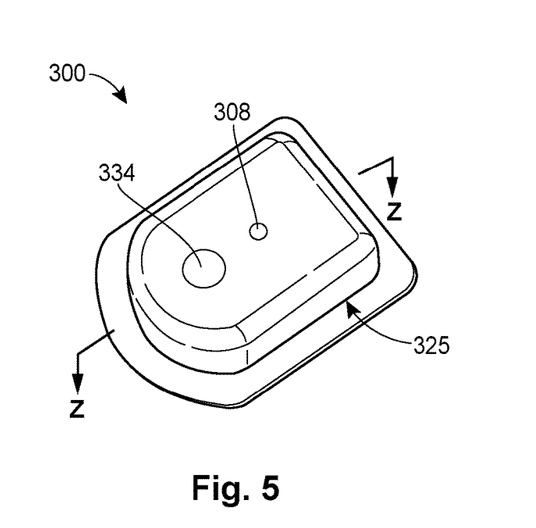
FIG. 5 is an exterior perspective view of a drug delivery system according to an embodiment of the present disclosure.
Figure 6:
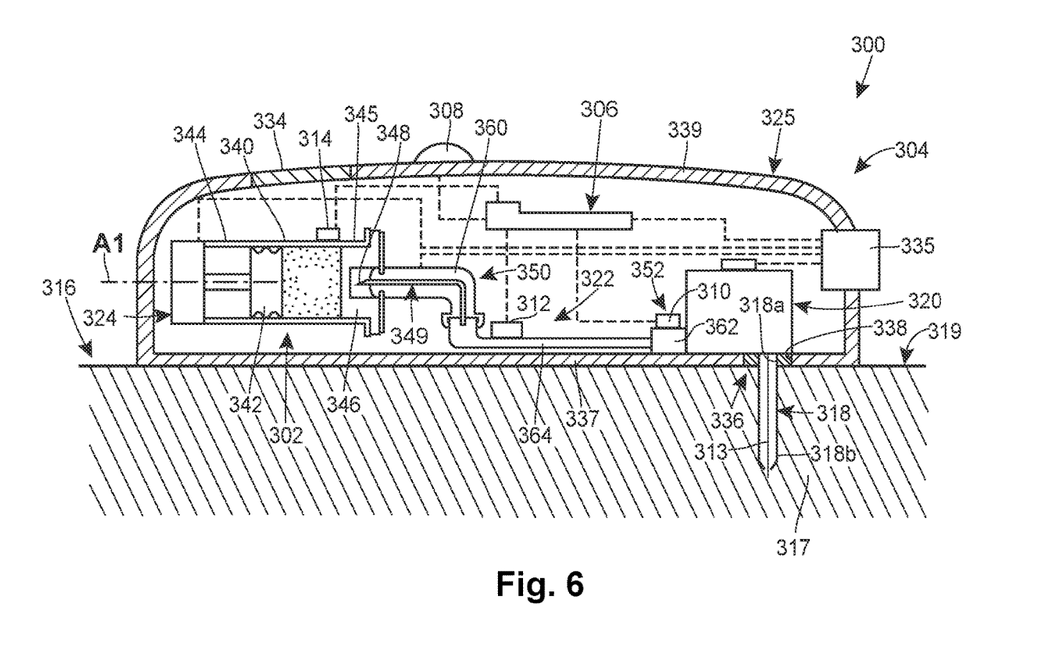
FIG. 6 is a schematic cross-sectional view of the drug delivery system depicted in FIG. 5 taken along line Z-Z.

Having described the structure and operation of the drug delivery system in general terms in connection with FIGS. 2-4, further exemplary details are provided regarding the reservoir, drug delivery device, pressures sensors, output device, and controller. In particular, an embodiment of a drug delivery system 300 incorporating the features of FIG. 2 and adding further details is illustrated in FIGS. 5 and 6. Similar elements are indicated by the same reference numerals as in FIG. 2, except incremented by 200. The drug delivery system 300 illustrated in FIGS. 5 and 6 may be operated in accordance with the methods described above in connection with FIGS. 2 and 3, or any other suitable method of operation.

Generally the drug delivery system 300 may be configured for injecting a drug into tissue (e.g., subcutaneous tissue, muscular tissue, etc.) of a patient 316. The drug may be, but is not limited to, various biologic drugs including peptides, peptibodies, and antibodies. The drug may be in a fluid or liquid form, and in certain formulations, may have a high viscosity. In some versions, the drug delivery system 300 may be configured to automatically deliver a fixed or a patient/operator-settable dose of the drug in the form of a bolus over a controlled or selected period of time. Furthermore, the drug delivery system 300 may be intended for self-administration by the patient, or may be operated by a formally-trained healthcare professional to administer the injection.

Various implementations and configurations of the drug delivery system 300 are possible. The drug delivery system 300 may be configured as a single-use, disposable injector, or alternatively, as a multiple-use reusable injector. In the embodiment illustrated in FIGS. 5 and 6, the drug delivery system 300 is configured as an on-body injector that is releasably attached to a patient's skin over the duration of an injection. In alternative embodiments, the drug delivery system can be configured as an autoinjector or pen-type injector that is held in the hand of a patient or user over the duration of the injection. In still further alternative embodiments, the drug delivery system can be a syringe that is manually operable to perform an injection, as opposed to the on-body injector and autoinjector versions where the drug delivery system may be able to automatically insert the administration member, automatically expel the drug from the reservoir, and/or automatically retract the administration member following the injection, and/or have other automated features or functions.

Referring to FIG. 6, the drug delivery system 300 may include a reservoir 302, a drug delivery device 304, a controller 306, an output device 308, a first pressure sensor 310, a second pressure sensor 312, and an end-of-dose sensor 314. The drug delivery device 304 may include an administration member 318, an insertion/retraction mechanism 320, a fluid pathway connection assembly 322, a drive assembly 324, and a main housing 325. In certain embodiments, each of the reservoir 302, controller 306, output device 308, first pressure sensor 310, second pressure sensor 312, end-of-dose sensor 314, administration member 318, insertion/retraction mechanism 320, fluid pathway connection assembly 322, drive assembly 324 may be disposed within an interior space of or mounted on an exterior of the main housing 325 during use of the drug delivery system 300.

The administration member 318 may be hollow and have a first end 318a connected or connectable in fluid communication with the reservoir 302 via the fluid pathway connection assembly 322, and a second end 318b to be inserted into tissue 317 of the patient 316. In some embodiments, the administration member 318 may take the form of a cannula made of a relatively flexible material and have a blunt tip at the second end 318b; whereas, in other embodiments, the administration member 318 may take the form of a needle constructed of a relatively rigid material and have a sharpened point at the second end 318b. The administration member 318 may be integrated with other elements of the drug delivery system 300, or the administration member 318 may be separate from the other elements of the drug delivery system 100 until immediately prior to use.

According to certain embodiments, including the one illustrated in FIG. 6, the drug delivery system 300 may further include a trocar or introducer member 313 to introduce the second end 318b of the administration member 318 into the patient's tissue 317, although this is not required according to each embodiment of the disclosure. The introducer member 313 may, in certain embodiments, be withdrawn back into the housing 325, thereby leaving the second end 318b of the administration member 318 inside the patient for a subcutaneous, intramuscular, etc. injection of the drug. In such embodiments, the administration member 318 may be a cannula (e.g., a blunt cannula) constructed of a relatively flexible or soft material such as plastic or another polymer, whereas the introducer member 313, which may be a solid or hollow needle or trocar, may be constructed a relatively rigid or hard material such as metal. Accordingly, the administration member 318 may be constructed of a more flexible material than introducer member 313. The relative flexibility of the administration member 318 may allow it to be disposed within the patient's tissue 317 for a period of a time (e.g., minutes, hours, days, etc.) without causing pain or significant discomfort to the patient. In other embodiments (not illustrated), the introducer member 313 may be omitted, and instead the insertion/retraction mechanism 320 may insert only the administration member 310 into the patient.

In certain embodiments, although the introducer member 313 may be retracted from the patient's tissue 317 prior drug delivery, the drug may pass through the introducer member 313 prior to being injected into the patient tissue 317. In such embodiments, the introducer member 313 may have a hollow interior passage which remains in fluid communication with and upstream of the administration member 318 after retraction of the introducer member 313. Accordingly, the drug may flow through the introducer member 313, then into the administration member 318, and finally into the patient's tissue 317. In this way, the introducer member 313 may be said to correspond to an administration member as it is at least momentarily inserted into the patient and is connected in fluid communication with the reservoir 302 during drug delivery, even though the drug may not exit the introducer member 313 directly into the patient.

Still referring to FIG. 6, an activation member 335 (e.g., a user-depressible button, touchscreen, microphone, etc.) may protrude through or otherwise be disposed at an exterior surface of the housing 325 and may be configured to initiate operation of drug delivery system 300 by activating, via mechanical and/or electrical means (shown in dotted lines in FIG. 6), the insertion/retraction mechanism 320, the fluid pathway connection assembly 322, the drive assembly 324, the controller 306, and/or other mechanisms and/or electronics. In embodiments where the activation member 335 is a button that is depressed or otherwise physically moved by a user or patient, the activation ember 335 may be configured to exert the motive force needed to activate the insertion/retraction mechanism 320, the fluid pathway connection assembly 322, the drive assembly 324, the controller 306, and/or other elements. In such embodiments, the activation member 335 may be physically connected to, either directly or indirectly via a mechanical linkage, the insertion/retraction mechanism 320, the fluid pathway connection assembly 322, the drive assembly 324, and/or other mechanisms such that manually depressing or otherwise interacting with the activation member 335 supplies the motive force necessary to activate these elements.

For example, in some embodiments, manually depressing the activation member 335 may cause the fluid pathway connection assembly 322 to move towards a stationarily-positioned reservoir 302, or alternatively, cause a movable reservoir 302 to move towards the stationarily-positioned fluid pathway connection assembly 322, and thereby cause a container access needles to penetrate through a seal member (e.g., a pierceable septum) into a drug-containing chamber of the reservoir 302. Additionally or alternatively, the activation member 335 may operate as an input device that transmits an electrical and/or mechanical signal to the controller 306, which in turn may execute programmable instructions to control operation of the insertion/retraction mechanism 320, the drive assembly 324, the fluid pathway connection assembly 322, and/or other elements. In such embodiments, the controller 306 may include a processor (e.g., a microprocessor) and a non-transitory memory for storing the programmable instructions to be executed by the processor. Furthermore, in such embodiments, the drive assembly 324 may include an internal actuator (e.g., an electric motor, a pneumatic or hydraulic pump, and/or a source of pressurized gas or liquid in the form of a propellant reservoir) which is separate from the activation member 335 and which, in response to an electrical control signal received from the controller 306, exert the motive force needed to activate the insertion/retraction mechanism 320, the fluid pathway connection assembly 322, and/or other elements.

With continued reference to FIG. 6, the housing 325 may include a bottom wall 337 configured to be releasably attached (e.g., adhered with an adhesive) to skin surface 319 of the patient 316, and a top wall 339 including an output device 308 and a window 334 for viewing the reservoir 302. The output device 308 controllable to notify and/or provide information to the patient or user about the operational state or condition of the drug delivery system 300. The output device 308 may be any device suitable for conveying information to the patient or user including a display (e.g., a liquid crystal display), a touchscreen, a light (e.g., a light emitting diode), a vibrator (e.g., an electro-mechanical vibrating element), a mechanical or color-changing flag member, a speaker, an alarm, and/or any other suitable device, or any combination thereof. One purpose of the output device 308 may be to alert the patient or user after dose completion that tissue back pressure remains above a certain threshold and thus the patient or user should wait to remove the administration member 318 from the patient's tissue 317, as described above.

An opening 336 may be formed in the bottom wall 337, and optionally a sterile barrier or seal member 338, such as a pierceable septum, may extend across the opening 336 to seal the interior of the housing 325 prior to use. In some embodiments, the seal member 338 may be omitted, and instead a removable sealing member (not illustrated) may cover and seal close the opening 336 prior to use.

After the bottom wall 337 of the housing 325 is attached to the patient's skin surface 319, the insertion/retraction mechanism 320 may be activated to automatically move the administration member 318, jointly together with the introducer member 313, from a retracted or storage position within the housing 325 to a deployed or operative position extending outside of the housing 325 as seen in FIG. 6. In the present embodiment, this may include the insertion/retraction mechanism 320 inserting the introducer member 313 and the administration member 318 surrounding the introducer member 313 through the seal member 338 and into the patient's tissue 317, as illustrated in FIG. 6. Immediately or shortly thereafter, the insertion/retraction mechanism 320 may automatically retract the introducer member 313, leaving the second end of the administration member 318 inside the patient for subcutaneous delivery of the drug from the reservoir 302. The introducer member 313 may be solid and have a sharpened end to assist with piercing the patient's skin surface 319.

In some embodiments, the insertion/retraction mechanism 320 may include one or more springs (e.g., helical compression springs, helical extension springs, helical torsion springs, spiral torsion springs, etc.) initially retained in an energized state, and which are released upon depression of the activation member 335 in order to insert the administration member 318 and the introducer member 313 into the patient. Furthermore, retraction of the introducer member 313 may be achieved by the automatic release of another spring included in the insertion/retraction mechanism 320 after the administration member 318 and the introducer member 313 have been inserted into the patient. Furthermore, at an appropriate time after drug delivery is complete, retraction of the administration member 318 from the patient's tissue 317 back inside the interior space of the housing 325 may be achieved by the automatic release of another spring included in the insertion/retraction mechanism 320. Other power sources for insertion and/or retraction are possible, including, for example, an electric motor, a hydraulic or pneumatic pump, or a canister that releases a pressurized gas or pressurized liquid to provide actuation energy.

Still referring to FIG. 6, the reservoir 302, which in some contexts may be referred to as a primary container, may include a wall 340 with an interior surface defining an interior space or chamber that is filled or fillable with the drug, and an exterior surface. In some embodiments, the reservoir 302 may be pre-filled with the drug by a drug manufacturer prior to installation of the reservoir 302 in the housing 325. In some embodiments, the reservoir 302 may be rigidly connected to the housing 325 such that the reservoir 302 cannot move relative to the housing; whereas, in other embodiments, the reservoir 302 may be slidably connected to the housing 325 such that the reservoir 302 can move relative to the housing 325 during operation of the drug delivery system 300. The reservoir 302 may have an elongate, barrel-like or cylindrical shape extending along a longitudinal axis A1. In some embodiments, the longitudinal axis A1 of the reservoir 302 may be perpendicular or substantially perpendicular, or otherwise non-parallel, to a direction in which the insertion/retraction mechanism 320 inserts the administration member 318 into the patient. This configuration may allow the on-body injector to have a generally planar, low-profile shape that can be worn by the patient without impeding movement of the patient's limbs. Initially, a stopper 342 or other plunger member may be positioned inside a proximal end 344 of the reservoir 302. The stopper 342 may sealingly and slidably engage the interior surface of the wall 340 of the reservoir 302, and may be movable relative to the wall 340 of the reservoir 302 to expel the drug from the reservoir 302.

The volume of the drug contained in the reservoir 302 may be: any volume in a range between approximately (e.g., ±10%) 0.5-50 mL, or any volume in a range between approximately (e.g., ±10%) 0.5-25 mL, any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3 mL, or any volume in a range between approximately (e.g., ±10%) 1-2.5 mL, or any volume equal to or greater than approximately (e.g., ±10%) 1 mL, or any volume equal to or greater than approximately (e.g., ±10%) 2.5 mL, or any volume equal to or greater than approximately (e.g., ±10%) 10 mL, or any volume equal to or greater than approximately (e.g., ±10%) 25 mL, or any volume equal to or greater than approximately (e.g., ±10%) 50 mL.

During operation of the drug delivery system 300, the drive assembly 318 may push the stopper 342 along the longitudinal axis A1 from the proximal end 344 to the distal end 345 of the reservoir 302 in order to expel drug from the reservoir 302. In some embodiments, the drive assembly 324 may include one or more springs (e.g., helical compression springs, helical extension springs, helical torsion springs, spiral torsion springs, etc.) initially retained in an energized state, and which are released upon depression of the activation member 335 and/or another actuator. Following their release, the spring(s) may expand or contract to move the stopper 342 through the reservoir 302 to expel the drug. In other embodiments, the drive assembly 324 may include an electric motor which rotates a gear mechanism, including for example one or more sprocket gears, to cause axial motion of the stopper 342 through the reservoir 302. In still further embodiments, the drive assembly 324 may include both an electric motor and spring(s), wherein the electric motor regulates expansion of the spring(s) via a tether or pulley system. In still further embodiments, the drive assembly 324 may include a canister that releases a pressurized gas or pressurized liquid to provide actuation energy.

At the distal end 345 of the reservoir 302, an opening may be formed in a distal end surface of the wall 340. The distal end surface may define a portion of the exterior surface of the wall 340. Prior to use of the drug delivery system 300, the opening may be covered and sealed closed by a sterile barrier or seal member 346, such as a pierceable septum, connected to the distal end 345 of the reservoir 302. Generally, the seal member 346 may be configured to selectively permit access to the drug-containing chamber of the reservoir 302. During operation of the drug delivery system 302, the seal member 346 may be physically altered (e.g., pierced) to permit fluid communication with the drug in the reservoir 302. In some embodiments, the seal member 346 may be constructed of a flexible or elastically deformable material such as rubber, for example, which is capable of being penetrated or pierced by, respectively, a sharpened end or point 348 of a container access needle 349 included as part of the fluid pathway connection assembly 322.

With continued reference to FIG. 6, the fluid pathway connection assembly 322 may be configured to selectively establish fluid communication between the reservoir 302 and the insertion/retraction mechanism 320 via a sterile fluid flow path during use of the drug delivery system 300. The fluid pathway connection assembly 322 may include an inlet end 350 connected or connectable in fluid communication with the reservoir 302, an outlet end 352 connected or connectable in fluid communication with the administration member 318. Prior to use of the drug delivery system 300, the fluid pathway connection assembly 322 may not be in fluid communication with the reservoir 302. During setup of the drug delivery system 300, or during operation of the drug delivery system 300 but prior to drug delivery, the user may manually, or the drug delivery system 300 may automatically, enable, connect, or open the necessary connections to establish fluid communication between the reservoir 302 and the administration member 318 via the fluid pathway connection assembly 322. Subsequently, the drive assembly 318 may move the stopper 342 in the distal direction to force the drug through the sterile fluid flow path of the fluid pathway connection assembly 322 and into the administration member 318 for delivery into the patient's tissue 317.

Still referring to FIG. 6, the inlet end 350 of the fluid pathway connection assembly 322 may include the container access needle 349. Prior to activation of the fluid pathway connection assembly 322, the container access needle 349 may be retained in a storage position wherein the proximal end of the container access needle 349 is disposed exterior to, and thus not in fluid communication with, the drug-containing chamber of the reservoir 302 (as seen in FIG. 6). After activation of the fluid pathway connection assembly 322, the container access needle 349 may move in a direction toward the reservoir 302 and into an operational position wherein the proximal end of the container access needle 349 is in fluid communication with the reservoir 302. Subsequently, the drive assembly 318 may move the stopper 342 in the distal direction to expel the drug through the container access needle 349, then through a sterile fluid flow path of the fluid pathway connection assembly 322, and then into the administration member 318 for injection into to the patient's tissue 317.

As shown in FIG. 6, the inlet end 350 of the fluid pathway connection assembly 322 may include by a first connection hub or fitting 360 connected or connectable in fluid communication with the reservoir 302, and the outlet end 252 of the fluid pathway connection assembly 322 may include a second connection hub or fitting 362 connected or connectable in fluid communication with the administration member 318 via the insertion/retraction mechanism 320. In alternative embodiments, the second connection hub 362 of the fluid pathway connection assembly 322 may be directly connected or connectable in fluid communication with the administration member 318. Extending between and connecting the first connection hub 360 and the second connection hub 362 is a tubular conduit 364. The tubular conduit 364 may, in certain embodiments, be formed entirely or partially by a flexible tube or other hollow elongate structure and may be constructed of a polymeric material such as plastic. In alternative embodiments, a portion of or the entirety of tubular conduit 364 may be made of a rigid material such as metal. Initially there may be slack in the tubular conduit 364 so as to allow the first connection hub 360 and/or the second connection hub 362 to move relative to the reservoir 302 and/or housing 325. Flexibility in the tubular conduit 364 may facilitate reservoir filling with standard fill-finish equipment and/or installation of the fluid pathway connection assembly 322 within the housing 325. The tubular conduit 364 may be a single, one-piece structure, or alternatively, formed by multiple interconnected structures.

The first connection hub 360 may provide a rigid mount for the container access needle 349, and may provide fluid communication between the container access needle 349 and the tubular conduit 364 during use of the drug delivery system, including drug delivery. In some embodiments, the container access needle may be rigidly or fixedly connected to the first connection hub 360 such that the container access needle 349 and the first connection hub 360 are immovable relative to each other and move together as a single unit during, for example, access of the drug-containing chamber of the reservoir 302 by the container access needle 349 during use of the drug delivery system 300.

Still referring to FIG. 6, the second connection hub 362 may provide fluid communication between the tubular conduit 364 and the administration member 210 during use of the drug delivery system, including drug delivery. According to some embodiments, the second connection hub 362 may provide a rigid mount for the administration member 318. In some embodiments, the administration member 318 may be rigidly or fixedly connected to the second connection hub 362 such that the administration member 318 and the second connection hub 362 are immovable relative to each other and move together as a single unit during, for example, insertion of the administration member 318 into the patient's tissue 317 and/or retraction of the administration member 318 from the patient's tissue 317.

According to some embodiments, the second connection hub 362 is rigid, whether according to the nature of the material that defines the second connection hub 362 or according to the nature of the structure of the second connection hub 362. The rigidity of the second connection hub 362 may allow it to hold an end of the tubular conduit 364 and the administration member 318 in a fixed orientation (e.g., a perpendicular or substantially perpendicular orientation) relative to each other during insertion and/or retraction movements. In some embodiments, the connection hub 362 may be constructed of a more rigid (i.e., less flexible) material than that which is used to construct the tubular conduit 364.

As illustrated in FIG. 6, the drug delivery system 300 may include a first pressure sensor 310 mounted adjacent the outlet end 352 of the fluid pathway connection assembly 322, a second pressure sensor 312 mounted adjacent the inlet end 350 of the fluid pathway connection assembly 322, and an end-of-dose sensor 314 mounted adjacent the distal end 345 of the reservoir 302. The first pressure sensor 310, the second pressure sensor 312, and the end-of-dose sensor 314 may be configured and/or operate in the same manner as, respectively, the first pressure sensor 110, the second pressure sensor 112, and the end-of-dose sensor 314 described above in connection with FIGS. 2-4. In FIG. 6, the first pressure sensor 310 and the second sensor 312 output respective signals representative of pressure measurements to the controller 306 via a wired connection, although alternative embodiments may involve a wireless connection. The end-of-dose sensor 314 may also output a signal indicative of the end-of-dose position of the stopper 342 to the controller 306 via a wired or wireless connection.

In certain alternative embodiments, the second pressure sensor 312 may be omitted, and both tissue back pressure and drive pressure measurements may be made via the first pressure sensor 310.

According to some embodiments, an internal passageway may be formed within the second connection hub 362. The internal passageway may be configured to provide direct fluid communication between an outlet of the tubular conduit 364 and an inlet of the administration member 318 during use of the drug delivery system, including drug delivery. In some embodiments, the internal passageway, or at least a portion thereof, may have a larger inner dimension (e.g., internal diameter) than the inlet of the administration member 318. The pressure sensor 310 may be mounted within or on an exterior of the second connection hub 362 such that the pressure sensor 310 is in fluid communication with the internal passageway of the second connection hub 362 at a location downstream of the outlet of the tubular conduit 364 and upstream of an inlet of the administration member 318.

In some embodiments, the pressure sensor 310 may be arranged immediately upstream of the inlet of the administration member 318 and downstream of the outlet of the tubular conduit 364. A direct or non-tortuous fluid flow path may exist between the pressure sensor 310 and the inlet of the administration member 318 by virtue of the pressure sensor 310 being arranged immediately upstream of the inlet of the administration member 318. In some embodiments, the distance between a sensing surface of the pressure sensor 310 and the inlet of the administration member 318 may be equal to or less than approximately (e.g., ±10%) 10 mm, or equal to or less than approximately (e.g., ±10%) 5 mm. Positioning the pressure sensor 310 immediately upstream of the inlet of the administration member 318 may allow the pressure sensor 310 to make more accurate measurements of tissue back pressure.

The second connection hub 362 may be operationally and/or structurally integrated with the insertion/retraction mechanism 320. Operation of the insertion/retraction mechanism 320 may cause the second connection hub 362 and any components mounted thereto to move relative to the patient and/or other elements of the drug delivery system such as the housing 325. For example, during insertion of the administration member 318 into the patient, the insertion/retraction mechanism 320 may cause the second connection hub 362, the pressure sensor 310, and the administration member 318 to move jointly together toward the patient and relative to the housing 325. During retraction of the administration member 318 from the patient, the insertion/retraction mechanism 320 may cause the second connection hub 362, the pressure sensor 310, and the administration member 318 to move jointly together away from the patient and relative to the housing 325.

While the foregoing embodiments of the drug delivery system have been described primarily in the context of an on-body injector that is adhered or otherwise attached to the patient's skin over the course of drug delivery, the scope of the present disclose is not limited to such wearable devices. In alternative embodiments, the drug delivery system may be configured as autoinjector or manually-powered syringe that is held in the patient's or user's hand over the course of drug delivery. In such alternative embodiments, the drug delivery system may have an elongate shape where a longitudinal axis of the drug reservoir is parallel to a longitudinal axis of the administration member.

As will be recognized, the systems, devices, and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

Drug Information

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the 0X40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery system comprising:
a reservoir filled or fillable with a drug;
a drug delivery device coupled to the reservoir to deliver the drug from the reservoir to a patient;
a pressure sensor;
an output device; and
a controller coupled to the pressure sensor and the output device, the controller being configured:
(a) to determine if the drug delivery device has completed delivering a dose of the drug to the patient, and if delivery of the dose of the drug is complete, to measure tissue back pressure using the pressure sensor, and
(b) to determine if the tissue back pressure is below a first predetermined value subsequent to (a), and if the tissue back pressure is below the first predetermined value, to control the output device at least once.

2. The drug delivery system of claim 1, comprising:
an administration member insertable into the patient and connected or connectable in fluid communication with the reservoir;
a mechanism configured to retract the administration member from the patient; and
wherein the controller is coupled to the mechanism and configured to control the mechanism to retract the administration member from the patient if the tissue back pressure is below the first predetermined value subsequent to (a).

3. The drug delivery system of claim 1, comprising:
an administration member insertable into the patient and connected or connectable in fluid communication with the reservoir; and
a drive assembly coupled to the controller and configured to actuate the reservoir to deliver the drug to the patient via the administration member.

4. The drug delivery system of claim 3, wherein the controller is configured to at least one of (i), (ii), (iii), or (iv):
(i) determine if a drive pressure exceeds a second predetermined value during drug delivery, and if the drive pressure exceeds the second predetermined value, to stop operation of the drive assembly,
(ii) determine if the drive pressure is below a third predetermined value during drug delivery, and if the drive pressure is below the third predetermined value, to stop operation of the drive assembly,
(iii) measure the drive pressure based on output from the pressure sensor, or
(iv) to determine if the tissue back pressure is below a fourth predetermined value prior to drug delivery, and if the tissue back pressure is below the fourth predetermined value, to prevent the drive assembly from actuating the reservoir to deliver the drug to the patient and/or control the output device at least once.

5. The drug delivery system of claim 3, comprising a second pressure sensor coupled to the controller, wherein the controller uses the second pressure sensor to measure drive pressure.

6. The drug delivery system of claim 5, wherein at least one of (i) or (ii):
(i) a minimum pressure which can be detected by the pressure sensor is lower than a minimum pressure which can be detected by the second pressure sensor, or
(ii) a maximum pressure which can be detected by the second pressure sensor is higher than a maximum pressure which can be detected by the pressure sensor.

7. The drug delivery system of claim 1, the drug delivery device comprising an administration member insertable into the patient, a tubular conduit connected or connectable in fluid communication with the reservoir, and a connection hub having an internal passageway configured to provide fluid communication between the tubular conduit and the administration member during drug delivery, and wherein the pressure sensor is disposed downstream of the tubular conduit, wherein the pressure sensor is mounted within or on an exterior of the connection hub.

8. The drug delivery system of claim 1, wherein the controller is configured to activate or deactivate the output device by transmitting communications to the output device if the tissue back pressure is below the first predetermined value.

9. A method comprising:
(i) providing the drug delivery system of claim 1;
(ii) operating the drug delivery device to deliver the dose of the drug to the patient;

(iii) determining if the drug delivery device has completed delivering the dose of the drug to the patient, and if delivery of the dose of the drug is complete, measuring tissue back pressure; and (iv) determining if tissue back pressure is below the first predetermined value subsequent to (iii), and if the tissue back pressure is below the first predetermined value, controlling the output device at least once.

10. The method of claim 9, comprising:

inserting an administration member into the patient with the drug delivery device prior to drug delivery; and operating the drug delivery device to retract the administration member from the patient if the tissue back pressure is below the first predetermined value subsequent to (iii).

11. The method of claim 9, comprising measuring drive pressure while operating the drug delivery device to deliver the dose of the drug to the patient; and at least one of (v) or (vi):

(v) determining if the drive pressure exceeds a second predetermined value, and if the drive pressure exceeds the second predetermined value, stopping drug delivery, or (vi) determining if the drive pressure is below a third predetermined value, and if the drive pressure is below the third predetermined value, stopping drug delivery.

12. The drug delivery system of claim 1, wherein the controller is configured to measure the tissue back pressure in response to and/or only after a determination that the drug delivery device has completed delivering the dose of the drug to the patient.

13. A drug delivery system comprising:

a reservoir filled or fillable with a drug;

a drug delivery device coupled to the reservoir to deliver the drug from the reservoir to a patient, the drug delivery device including an administration member insertable into the patient and a mechanism configured to retract the administration member from the patient;

a pressure sensor; and a controller coupled to the pressure sensor and the drug delivery device, the controller being configured:

(a) to determine if the drug delivery device has completed delivering a dose of the drug to the patient, and if delivery of the dose of the drug is complete, to measure tissue back pressure using the pressure sensor, and (b) to determine if the tissue back pressure is below a first predetermined value subsequent to (a), and if the tissue back pressure is below the first predetermined value, to control the mechanism to retract the administration member from the patient.

14. The drug delivery system of claim 13, comprising a drive assembly coupled to the controller and configured to actuate the reservoir to deliver the drug to the patient via the administration member, and wherein the controller is configured to at least one of (i), (ii), (iii), or (iv):

(i) determine if a drive pressure exceeds a second predetermined value during drug delivery, and if the drive pressure exceeds the second predetermined value, to stop operation of the drive assembly, (ii) determine if the drive pressure is below a third predetermined value during drug delivery, and if the drive pressure is below the third predetermined value, to stop operation of the drive assembly, (iii) measure the drive pressure based on output from the pressure sensor, or (iv) determine if the tissue back pressure is below a fourth predetermined value prior to drug delivery, and if the tissue back pressure is below the fourth predetermined value, to prevent the drive assembly from actuating the reservoir to deliver the drug to the patient.

15. The drug delivery system of claim 14, comprising a second pressure sensor coupled to the controller, wherein the controller uses the second pressure sensor to measure drive pressure.

16. The drug delivery system of claim 15, wherein at least one of (i) or (ii):

(i) a minimum pressure which can be detected by the pressure sensor is lower than a minimum pressure which can be detected by the second pressure sensor, or (ii) a maximum pressure which can be detected by the second pressure sensor is higher than a maximum pressure which can be detected by the pressure sensor.

17. The drug delivery system of claim 13, the drug delivery device comprising a tubular conduit connected or connectable in fluid communication with the reservoir, and a connection hub having an internal passageway configured to provide fluid communication between the tubular conduit and the administration member during drug delivery, and wherein the pressure sensor is disposed downstream of the tubular conduit, and wherein the pressure sensor is mounted within or on an exterior of the connection hub.

18. A method comprising:

(i) providing the drug delivery system of claim 13;

(ii) inserting the administration member of the drug delivery device into the patient;

(iii) operating the drug delivery device to deliver the dose of the drug stored in the reservoir to the patient via the administration member;

(iv) determining if the drug delivery device has completed delivering the dose of the drug to the patient, and if delivery of the dose of the drug is complete, measuring tissue back pressure; and (v) determining if tissue back pressure is below the first predetermined value subsequent to (iv), and if the tissue back pressure is below the first predetermined value, operating the drug delivery device to retract the administration member from the patient.

19. The method of claim 18, comprising at least one of (A) and (B):

(A) (vi) measuring drive pressure while operating the drug delivery device to deliver the dose of the drug to the patient; and (vii) determining if the drive pressure exceeds a second predetermined value, and if the drive pressure exceeds the second predetermined value, stopping drug delivery, or (B) (viii) measuring drive pressure while operating the drug delivery device to deliver the dose of the drug to the patient; and (ix) determining if the drive pressure is below a third predetermined value, and if the drive pressure is below the third predetermined value, stopping drug delivery.

20. The drug delivery system of claim 13, wherein the controller is configured to measure the tissue back pressure in response to and/or only after a determination that the drug delivery device has completed delivering the dose of the drug to the patient.

* * * * *